US012414691B1

(12) United States Patent
Nash et al.

(10) Patent No.: US 12,414,691 B1
(45) Date of Patent: Sep. 16, 2025

(54) EYE MONITORING AND PROTECTION

(71) Applicant: UIPCO, LLC, San Antonio, TX (US)

(72) Inventors: Justin Royell Nash, Little Elm, TX (US); Ivan Ortiz, Little Elm, TX (US); Austin Ray Keeton, The Colony, TX (US); Subhalakshmi Selvam, Allen, TX (US); Fang Yuan Gonzalez, Frisco, TX (US); Huihui Wu, Grapevine, TX (US); Salvador Adrian Bretado, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 853 days.

(21) Appl. No.: 17/678,497

(22) Filed: Feb. 23, 2022

(51) Int. Cl.
*A61B 3/113* (2006.01)
*A61H 5/00* (2006.01)
*G06F 3/01* (2006.01)

(52) U.S. Cl.
CPC ............... *A61B 3/113* (2013.01); *A61H 5/00* (2013.01); *G06F 3/013* (2013.01); *G06F 3/014* (2013.01); *A61H 2201/1604* (2013.01)

(58) Field of Classification Search
None
See application file for complete search history.

(56) References Cited

U.S. PATENT DOCUMENTS

| | | | |
|---|---|---|---|
| 11,296,971 B1 | 4/2022 | Jain et al. | |
| 12,029,688 B1 * | 7/2024 | Frank | A61F 9/029 |
| 12,114,931 B2 * | 10/2024 | Dana | A61B 3/0025 |
| 2019/0008448 A1 | 1/2019 | Begtrup et al. | |
| 2019/0030230 A1 | 1/2019 | Connor | |
| 2019/0038129 A1 * | 2/2019 | Ong | G06V 40/161 |
| 2019/0117083 A1 | 4/2019 | Wang et al. | |
| 2019/0191998 A1 | 6/2019 | Heikenfeld et al. | |
| 2020/0218342 A1 * | 7/2020 | Murali | G02B 27/0093 |
| 2020/0229973 A1 * | 7/2020 | Tsubota | B05B 17/0676 |
| 2021/0369103 A1 * | 12/2021 | Zhang | A61B 3/0025 |

(Continued)

OTHER PUBLICATIONS

Song et al., Self-Powered Wearable Biosensors, ACS Partner Journal, received Jan. 4, 2021, revised Jan. 28, 2021, https://dx.doi.org/10.1021/accountsmr.1c00002?ref=pdf.

(Continued)

*Primary Examiner* — Robert E. Tallman
(74) *Attorney, Agent, or Firm* — Potomac Law Group, PLLC; Dannon G. Allbee

(57) ABSTRACT

An eye-monitoring system monitors and relieves, or even prevents, eye fatigue in users of display screens. The system monitors indicia of eye fatigue in the user, analyzes whatever information the monitoring uncovers, and assigns a score to the monitored indicia. For example, rubbing the eyes is a pretty strong sign of eye fatigue, while the system may have to monitor pupil dilation for quite a while to decide that eye fatigue is likely. The assigned score is associated with the likelihood that the user has, or will soon have, eye fatigue. If the score so warrants, then the system takes remedial action to lessen any current fatigue and to hold off the development of more fatigue. As an example of remedial action, the system alters the visual content seen by the user to shift the content's color palette slightly or to decrease its displayed brightness.

20 Claims, 11 Drawing Sheets

(56) References Cited

U.S. PATENT DOCUMENTS

| | | | | |
|---|---|---|---|---|
| 2022/0217325 A1* | 7/2022 | Lee | ............... | G06V 40/19 |
| 2022/0331550 A1* | 10/2022 | Yang | ............... | A61F 9/04 |
| 2023/0111835 A1* | 4/2023 | Balsam | ............... | A61B 3/10 |
| | | | | 345/589 |
| 2023/0355433 A1* | 11/2023 | Zhang | ............... | A61F 9/0026 |

OTHER PUBLICATIONS

Zhao et al., A Fully Integrated and Self-Powered Smartwatch for Continuous Sweat Glucose Monitoring, ACS Sens. 2019, 4, pp. 1925-1933, published Jul. 4, 2019.

D. P. Rose et al., "Adhesive RFID Sensor Patch for Monitoring of Sweat Electrolytes," in IEEE Transactions on Biomedical Engineering, vol. 62, No. 6, pp. 1457-1465, Jun. 2015, doi: 10.1109/TBME.2014.2369991, downloaded from https://ieeexplore.ieee.org/document/6953152 on Feb. 6, 2025 (Year: 2015).

Shen et al., Point-of-care colorimetric detection with a smartphone, Lab on a Chip journal, 2012, 12, pp. 4240-4243, downloaded Feb. 3, 2025 from https://pubs.rsc.org/en/content/articlelanding/2012/lc/c2lc40741h, DOI: 10.1039/c2lc40741h (Year: 2012).

\* cited by examiner

EYE MONITORING AND PROTECTION

TECHNICAL FIELD

The present disclosure is directed to preventing and relieving eye fatigue of users of visual displays.

BACKGROUND

Modern electronic devices such as televisions, smartphones, and head-mounted displays ("HMDs") often subject their users to eye fatigue. Their displays direct bright light into the user's eyes, and users often watch these displays for hours per day.

Artificial reality ("XR") technologies (of all sorts including enhanced reality: see below) exacerbate this problem with content that regularly tempts a user to direct her eyes rapidly from one portion of the display to another and to the extremes of the user's eye range. These wide eye swings, when coupled with long periods of use and the bright light of the HMD, fatigue eyes more quickly than commonly occurs in the real world. XR's compelling content often keeps a user transfixed, ignoring early signs of eye fatigue, until the fatigue produces headaches, visual blurriness, or other nuisances.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

DETAILED DESCRIPTION

Figure 1:
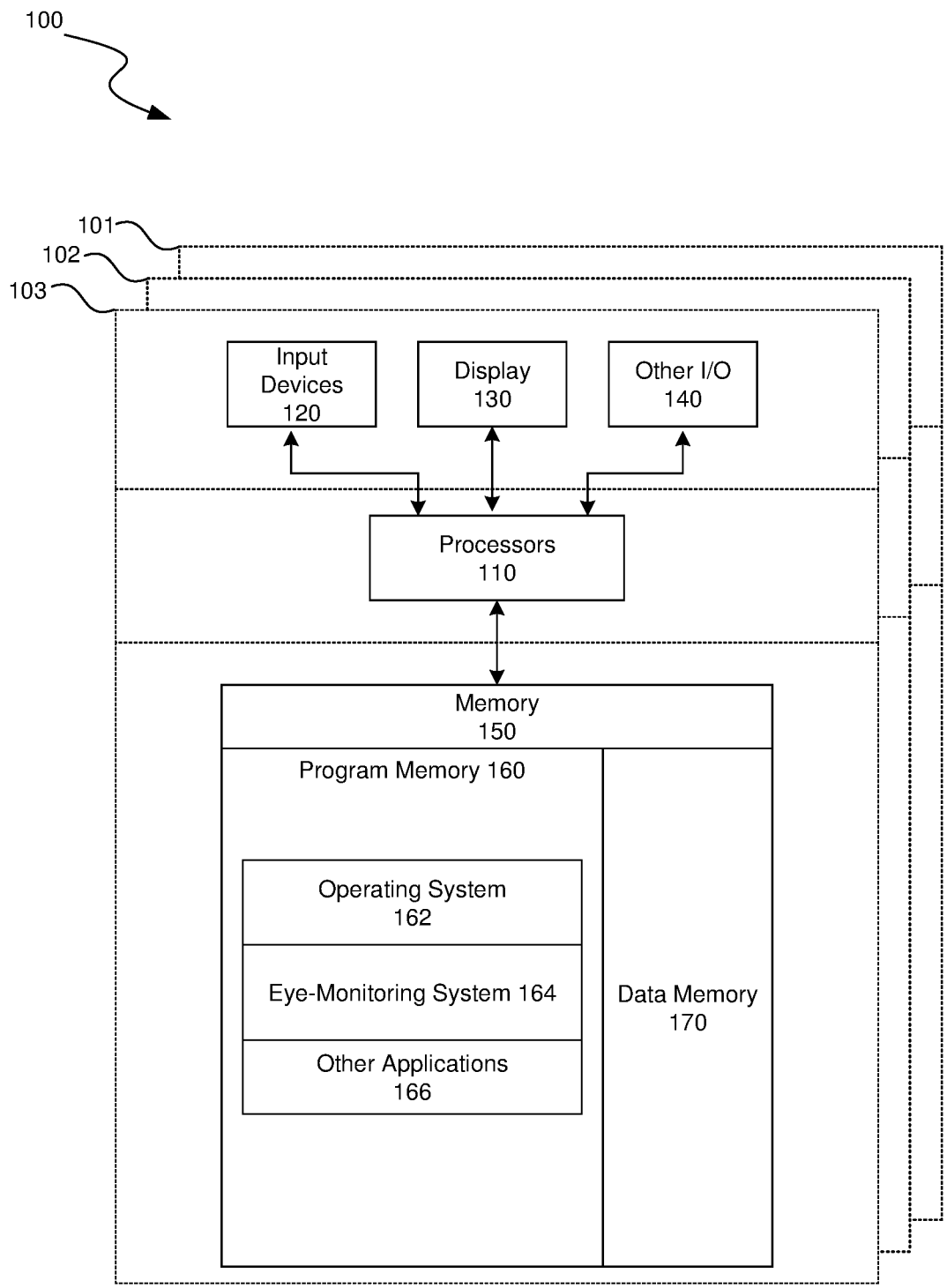
FIG. 1 is a block diagram illustrating an overview of devices on which some implementations of the present technology can operate.

Aspects of the present disclosure are directed to an eye-monitoring system that monitors and relieves, or even prevents, eye fatigue in users of display screens. The system monitors indicia of eye fatigue in the user and computes a score associated with the likelihood that the user has, or will soon have, eye fatigue. If the score so warrants, the system takes remedial action to lessen any current fatigue and hold off the development of more fatigue.

Depending upon the resources at its disposal, the system may simultaneously monitor several indicia of eye fatigue. A camera focused on the area around and including the user's eyes can watch for bloodshot eyes (e.g., the eye color becoming more red), for an amount of swelling or redness near the eye, for pupil dilation, or for an increased amount of blood flow near the eye. This camera may be part of the eye-tracking system of an HMD, in which case it can also measure an amount of eye movement, how often the eyes move toward their range limits, and an amount of time the eyes are used (i.e., how long the HMD is in use). Other monitoring can determine a level of eye moisture or an eye temperature.

The system's camera can also determine the color and brightness of the content viewed by the user. If the system is connected to a display device, such as an artificial reality device, then this information may be monitored without the need of a separate camera. Using input from a body tracking and/or eye tracking system of the artificial reality device, the eye-monitoring system can also detect when the user makes a gesture indicative of eye fatigue, such as rubbing the eyes or the muscles around the eyes.

The eye-monitoring system analyzes whatever information the monitoring uncovers and assigns a score to the monitored indicia. For example, rubbing the eyes is a pretty strong sign of eye fatigue, while the system may have to monitor changes in pupil dilation for quite a while to decide that eye fatigue is likely.

When the fatigue score is such that a remediation action is called for, the eye-monitoring system may choose one or more actions, again depending upon the resources at its disposal. One system may include "spritzers" that directly apply a small amount of a moisturizing agent to the fatigued eyes. Another system may have motor-driven muscle massagers in touch with the area around the eyes. The massage may lessen the fatigue in those muscles.

When the eye-monitoring system is connected to a display system that provides visual content to the user, then the eye-monitoring system can take a remediation action that tells the display system to alter its content. For example, a long period of viewing content with strong blue can be fatiguing, so the eye-monitoring system tells the display system to shift the content's color palette slightly toward red. The system can also decrease the brightness of the display or reduce the viewable area (so the user's eye will not move to the extremes of its range as often).

In addition to the above remediation procedures, the eye-monitoring system can send a message to the user warning of eye fatigue. The screen that the user is currently viewing may display the warning message, an artificial reality device may play an audio warning, etc.

As alluded to above, the present technology can be fully integrated into XR systems. The XR system's eye-tracking system is augmented to monitor many of the eye-fatigue indicia. The XR system's display system alters aspects of its content (brightness, color palette, viewable area) to lessen eye fatigue.

Thus, the eye-monitoring system, in various implementations, can be configured to detect current or incipient eye fatigue. The remediation actions can lessen eye fatigue or at least warn the user to take a break from viewing for a while to let her eyes rest. As described below, these aspects of the present technology build on existing computer systems to enhance the utility of these systems for all users.

Embodiments of the disclosed technology may include or be implemented in conjunction with an artificial reality system. Artificial reality or extra reality (XR) is a form of reality that has been adjusted in some manner before presentation to a user, which may include, e.g., virtual reality (VR), augmented reality (AR), mixed reality (MR), hybrid reality, or some combination and/or derivatives thereof. Artificial reality content may include completely generated content or generated content combined with captured content (e.g., real-world photographs). The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may be associated with applications, products, accessories, services, or some combination thereof, that are, e.g., used to create content in an artificial reality and/or used in (e.g., perform activities in) an artificial reality. The artificial reality system that provides the artificial reality content may be implemented on various platforms, including a head-mounted display (HMD) connected to a host computer system, a standalone HMD, a mobile device or computing system, a "cave" environment or other projection system, or any other hardware platform capable of providing artificial reality content to one or more viewers.

"Virtual reality" or "VR," as used herein, refers to an immersive experience where a user's visual input is controlled by a computing system. "Augmented reality" or "AR" refers to systems where a user views images of the real world after they have passed through a computing system. For example, a tablet with a camera on the back can capture images of the real world and then display the images on the screen on the opposite side of the tablet from the camera. The tablet can process and adjust or "augment" the images as they pass through the system, such as by adding virtual objects. "Mixed reality" or "MR" refers to systems where light entering a user's eye is partially generated by a computing system and partially composes light reflected off objects in the real world. For example, a MR headset could be shaped as a pair of glasses with a pass-through display, which allows light from the real world to pass through a waveguide that simultaneously emits light from a projector in the MR headset, allowing the MR headset to present virtual objects intermixed with the real objects the user can see. "Artificial reality," "extra reality," or "XR," as used herein, refers to any of VR, AR, MR, or any combination or hybrid thereof.

Previous display systems do not address eye fatigue. They neither detect eye fatigue nor provide remediation actions to combat it. With these systems, a user is on his own to know to lessen viewing time or do anything else to reduce eye fatigue. The eye-monitoring system and methods disclosed herein are expected to overcome these deficiencies in existing systems. The system addresses multiple aspects of eye fatigue, including dryness, muscle fatigue, and over-stimulation. Because it considers both aspects of the user's physical condition and aspects of the user's viewing environment, the system's remediations are more comprehensively based than those produced by previous systems whether automated or fully human controlled. By monitoring and addressing eye fatigue, often alleviating it without conscious intervention on the part of the user, the eye-monitoring system expands the fatigue-less scope of use of display systems.

Several implementations are discussed below in more detail in reference to the figures. FIG. 1 is a block diagram illustrating an overview of devices on which some implementations of the disclosed technology can operate. The devices can comprise hardware components of a computing system 100 that monitors eye fatigue. In various implementations, computing system 100 can include a single computing device 103 or multiple computing devices (e.g., computing device 101, computing device 102, and computing device 103) that communicate over wired or wireless channels to distribute processing and share input data. In some implementations, computing system 100 can include a stand-alone headset capable of providing a computer created or augmented experience for a user without the need for external processing or sensors. In other implementations, computing system 100 can include multiple computing devices such as a headset and a core processing component (such as a console, mobile device, or server system) where some processing operations are performed on the headset and others are offloaded to the core processing component. Example headsets are described below in relation to FIGS. 2A and 2B. In some implementations, position and environment data can be gathered only by sensors incorporated in the headset device, while in other implementations one or more of the non-headset computing devices can include sensor components that can track environment or position data.

Computing system 100 can include one or more processor(s) 110 (e.g., central processing units (CPUs), graphical processing units (GPUs), holographic processing units (HPUs), etc.) Processors 110 can be a single processing unit or multiple processing units in a device or distributed across multiple devices (e.g., distributed across two or more of computing devices 101-103).

Computing system 100 can include one or more input devices 120 that provide input to the processors 110, notifying them of actions. The actions can be mediated by a hardware controller that interprets the signals received from the input device and communicates the information to the processors 110 using a communication protocol. Each input device 120 can include, for example, a mouse, a keyboard, a touchscreen, a touchpad, a wearable input device (e.g., a haptics glove, a bracelet, a ring, an earring, a necklace, a watch, etc.), a camera (or other light-based input device, e.g., an infrared sensor), a microphone, or other user input devices.

Processors 110 can be coupled to other hardware devices, for example, with the use of an internal or external bus, such as a PCI bus, SCSI bus, or wireless connection. The processors 110 can communicate with a hardware controller for devices, such as for a display 130. Display 130 can be used to display text and graphics. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network chip or card, video chip or card, audio chip or card, USB, firewire or other external device, camera, printer, speakers, CD-ROM drive, DVD drive, disk drive, etc.

In some implementations, input from the I/O devices 140, such as cameras, depth sensors, IMU sensor, GPS units, LiDAR or other time-of-flights sensors, etc. can be used by the computing system 100 to identify and map the physical environment of the user while tracking the user's location within that environment. This simultaneous localization and mapping (SLAM) system can generate maps (e.g., topologies, girds, etc.) for an area (which may be a room, building, outdoor space, etc.) and/or obtain maps previously generated by computing system 100 or another computing system that had mapped the area. The SLAM system can track the user within the area based on factors such as GPS data, matching identified objects and structures to mapped objects and structures, monitoring acceleration and other position changes, etc.

Computing system 100 can include a communication device capable of communicating wirelessly or wire-based with other local computing devices or a network node. The communication device can communicate with another device or a server through a network using, for example, TCP/IP protocols. Computing system 100 can utilize the communication device to distribute operations across multiple network devices.

The processors 110 can have access to a memory 150, which can be contained on one of the computing devices of computing system 100 or can be distributed across the multiple computing devices of computing system 100 or other external devices. A memory includes one or more hardware devices for volatile or non-volatile storage, and can include both read-only and writable memory. For example, a memory can include one or more of random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 150 can include program memory 160 that stores programs and software, such as an operating system 162, an eye-monitoring system 164, and other application programs 166. Memory 150 can also include data memory 170 that can include, e.g., histories of eye use, virtual models mapping real and virtual locations of object and users, environmental data, configuration data, settings, user options or preferences, etc., which can be provided to the program memory 160 or any element of the computing system 100.

Some implementations can be operational with numerous other computing system environments or configurations. Examples of computing systems, environments, and/or configurations that may be suitable for use with the technology include, but are not limited to, XR headsets, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2A:
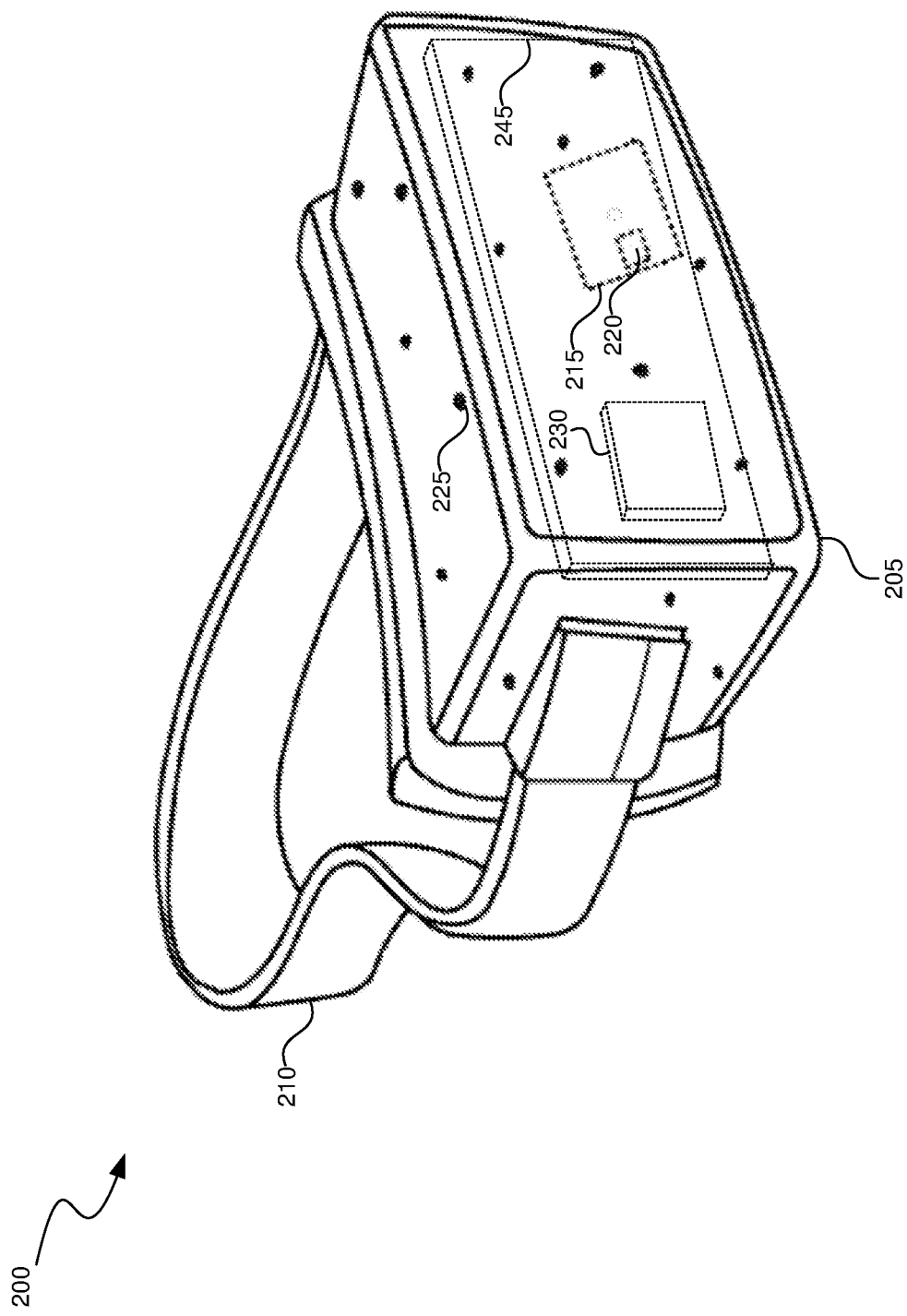
FIG. 2A is a wire diagram illustrating a virtual reality headset which can be used in some implementations of the present technology.

FIG. 2A is a wire diagram of a virtual reality head-mounted display (HMD) 200, in accordance with some embodiments. The HMD 200 includes a front rigid body 205 and a band 210. The front rigid body 205 includes one or more electronic display elements of an electronic display 245, an inertial motion unit (IMU) 215, one or more position sensors 220, locators 225, and one or more compute units 230. The position sensors 220, the IMU 215, and compute units 230 may be internal to the HMD 200 and may not be visible to the user. In various implementations, the IMU 215, position sensors 220, and locators 225 can track movement and location of the HMD 200 in the real world and in an artificial reality environment in three degrees of freedom (3DoF) or six degrees of freedom (6DoF). For example, the locators 225 can emit infrared light beams which create light points on real objects around the HMD 200. As another example, the IMU 215 can include e.g., one or more accelerometers, gyroscopes, magnetometers, other non-camera-based position, force, or orientation sensors, or combinations thereof. One or more cameras (not shown) integrated with the HMD 200 can detect the light points. Compute units 230 in the HMD 200 can use the detected light points to extrapolate position and movement of the HMD 200 as well as to identify the shape and position of the real objects surrounding the HMD 200.

The electronic display 245 can be integrated with the front rigid body 205 and can provide image light to a user as dictated by the compute units 230. In various embodiments, the electronic display 245 can be a single electronic display or multiple electronic displays (e.g., a display for each user eye). Examples of the electronic display 245 include: a liquid crystal display (LCD), an organic light-emitting diode (OLED) display, an active-matrix organic light-emitting diode display (AMOLED), a display including one or more quantum dot light-emitting diode (QOLED) sub-pixels, a projector unit (e.g., microLED, LASER, etc.), some other display, or some combination thereof.

In some implementations, the HMD 200 can be coupled to a core processing component such as a personal computer (PC) (not shown) and/or one or more external sensors (not shown). The external sensors can monitor the HMD 200 (e.g., via light emitted from the HMD 200) which the PC can use, in combination with output from the IMU 215 and position sensors 220, to determine the location and movement of the HMD 200.

Figure 2B:
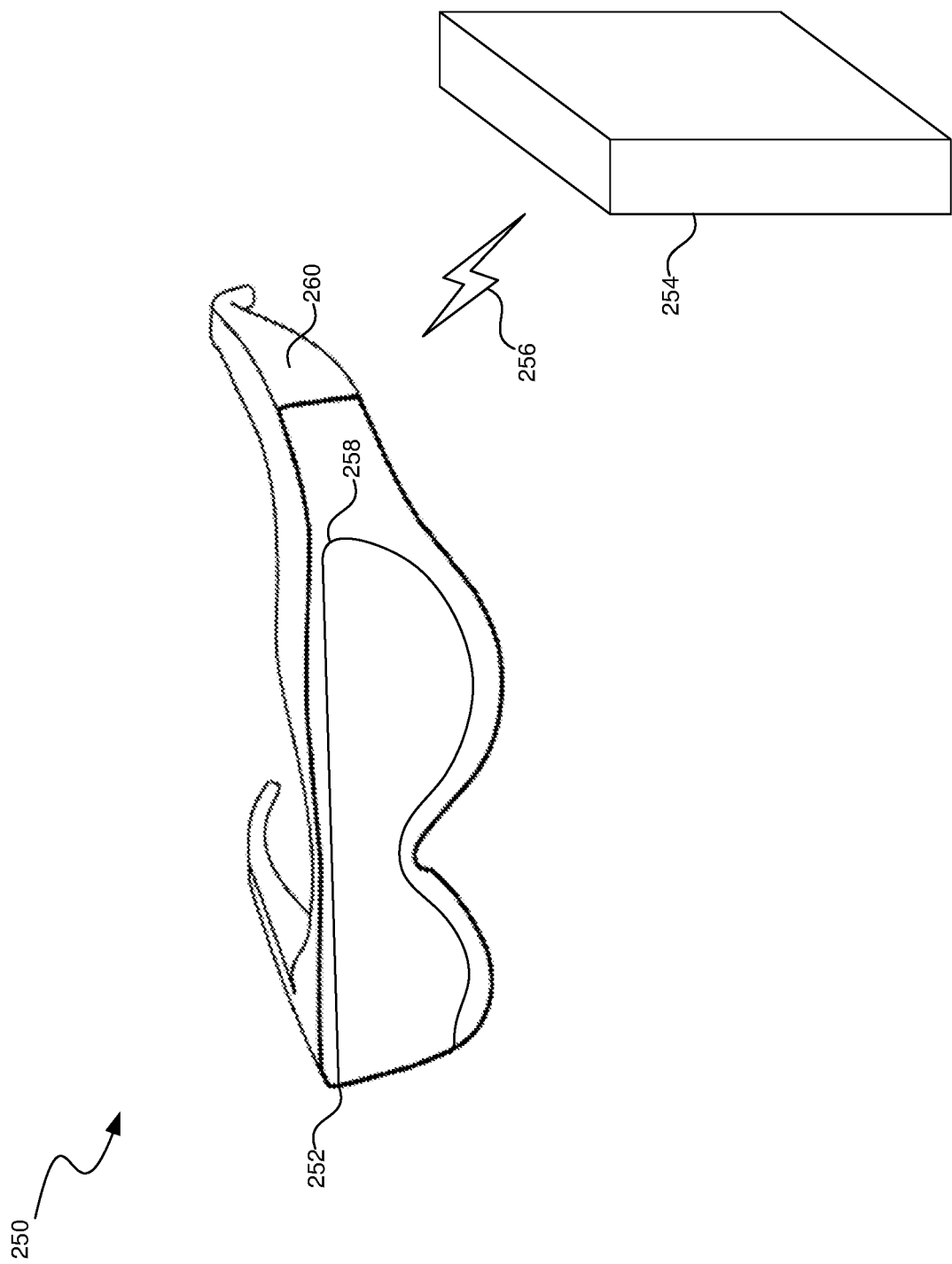
FIG. 2B is a wire diagram illustrating a mixed reality headset which can be used in some implementations of the present technology.

FIG. 2B is a wire diagram of a mixed reality HMD system 250 which includes a mixed reality HMD 252 and a core processing component 254. The mixed reality HMD 252 and the core processing component 254 can communicate via a wireless connection (e.g., a 60 GHz link) as indicated by link 256. In other implementations, the mixed reality system 250 includes a headset only, without an external compute device or includes other wired or wireless connections between the mixed reality HMD 252 and the core processing component 254. The mixed reality HMD 252 includes a pass-through display 258 and a frame 260. The frame 260 can house various electronic components (not shown) such as light projectors (e.g., LASERs, LEDs, etc.), cameras, eye-tracking sensors, MEMS components, networking components, etc.

The projectors can be coupled to the pass-through display 258, e.g., via optical elements, to display media to a user. The optical elements can include one or more waveguide assemblies, reflectors, lenses, mirrors, collimators, gratings, etc., for directing light from the projectors to a user's eye. Image data can be transmitted from the core processing component 254 via link 256 to HMD 252. Controllers in the HMD 252 can convert the image data into light pulses from the projectors, which can be transmitted via the optical elements as output light to the user's eye. The output light can mix with light that passes through the display 258, allowing the output light to present virtual objects that appear as if they exist in the real world.

Similarly to the HMD 200, the HMD system 250 can also include motion and position tracking units, cameras, light sources, etc., which allow the HMD system 250 to, e.g., track itself in 3DoF or 6DoF, track portions of the user (e.g., hands, feet, head, or other body parts), map virtual objects to appear as stationary as the HMD 252 moves, and have virtual objects react to gestures and other real-world objects.

Figure 2C:
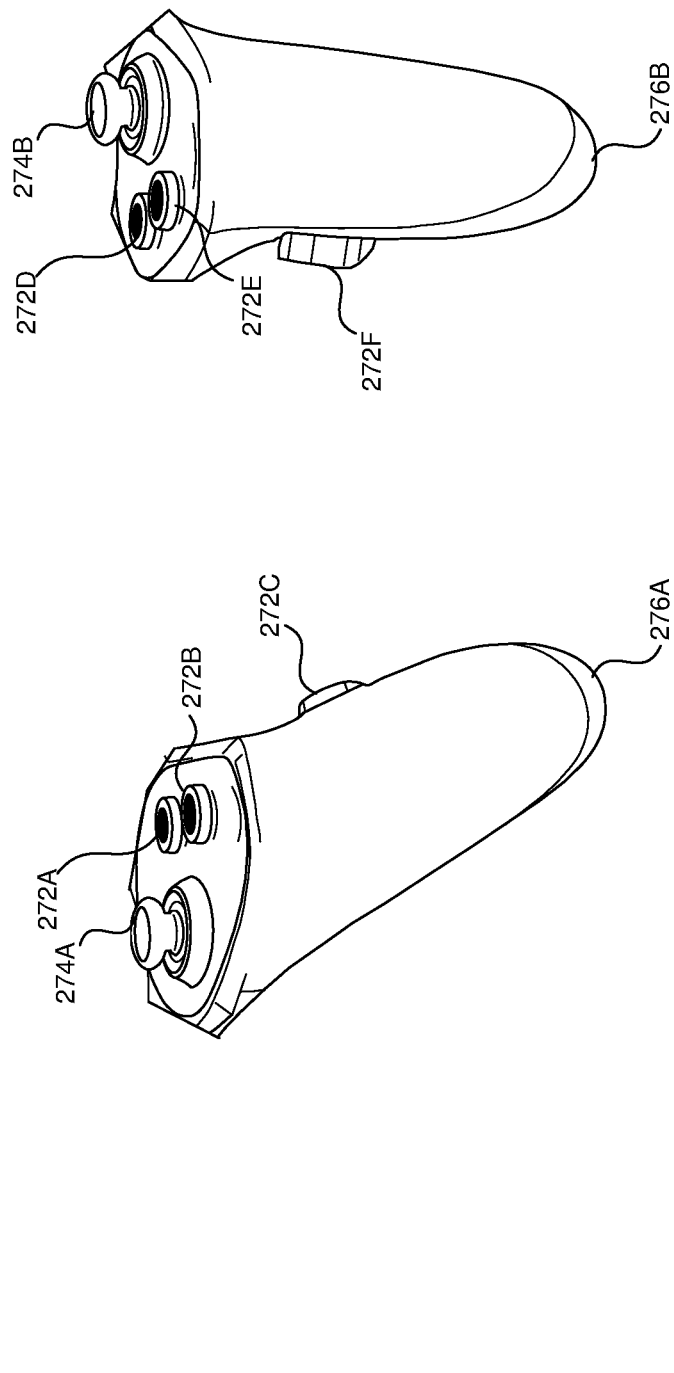
FIG. 2C is a wire diagram illustrating controllers which, in some implementations, a user can hold in one or both hands to interact with an artificial reality environment.

FIG. 2C illustrates controllers 270, which, in some implementations, a user can hold in one or both hands to interact with an artificial reality environment presented by the HMD 200 and/or HMD 250. The controllers 270 can be in communication with the HMDs, either directly or via an external device (e.g., core processing component 254). The controllers can have their own IMU units, position sensors, and/or can emit further light points. The HMD 200 or 250, external sensors, or sensors in the controllers can track these controller light points to determine the controller positions and/or orientations (e.g., to track the controllers in 3DoF or 6DoF). The compute units 230 in the HMD 200 or the core processing component 254 can use this tracking, in combination with IMU and position output, to monitor hand positions and motions of the user. The controllers can also include various buttons (e.g., buttons 272A-F) and/or joysticks (e.g., joysticks 274A-B), which a user can actuate to provide input and interact with objects.

In various implementations, the HMD 200 or 250 can also include additional subsystems, such as an eye tracking unit, an audio system, various network components, etc., to monitor indications of user interactions and intentions. For example, in some implementations, instead of or in addition to controllers, one or more cameras included in the HMD 200 or 250, or from external cameras, can monitor the positions and poses of the user's hands to determine gestures and other hand and body motions. As another example, one or more light sources can illuminate either or both of the user's eyes and the HMD 200 or 250 can use eye-facing cameras to capture a reflection of this light to determine eye position (e.g., based on set of reflections around the user's cornea), modeling the user's eye and determining a gaze direction.

Figure 3:
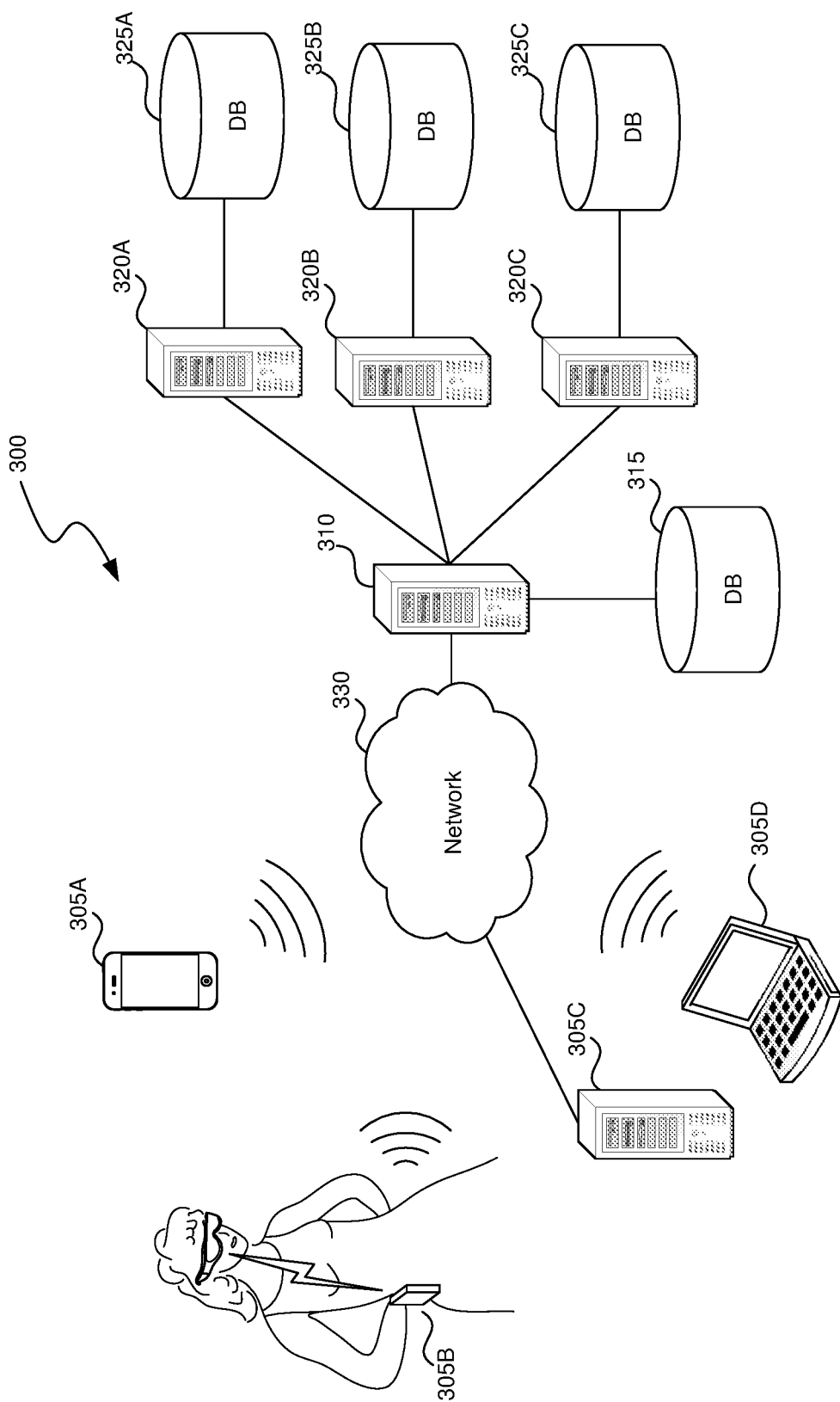
FIG. 3 is a block diagram illustrating an overview of an environment in which some implementations of the present technology can operate.

FIG. 3 is a block diagram illustrating an overview of an environment 300 in which some implementations of the disclosed technology can operate. Environment 300 can include one or more client computing devices 305A-D, examples of which can include computing system 100. In some implementations, some of the client computing devices (e.g., client computing device 305B) can be the HMD 200 or the HMD system 250. Client computing devices 305 can operate in a networked environment using logical connections through network 330 to one or more remote computers, such as a server computing device.

In some implementations, server 310 can be an edge server which receives client requests and coordinates fulfillment of those requests through other servers, such as servers 320A-C. Server computing devices 310 and 320 can comprise computing systems, such as computing system 100. Though each server computing device 310 and 320 is displayed logically as a single server, server computing devices can each be a distributed computing environment encompassing multiple computing devices located at the same or at geographically disparate physical locations.

Client computing devices 305 and server computing devices 310 and 320 can each act as a server or client to other server/client device(s). Server 310 can connect to a database 315. Servers 320A-C can each connect to a corresponding database 325A-C. As discussed above, each server 310 or 320 can correspond to a group of servers, and each of these servers can share a database or can have its own database. Though databases 315 and 325 are displayed logically as single units, databases 315 and 325 can each be a distributed computing environment encompassing multiple computing devices, can be located within their corresponding server, or can be located at the same or at geographically disparate physical locations.

Network 330 can be a local area network (LAN), a wide area network (WAN), a mesh network, a hybrid network, or other wired or wireless networks. Network 330 may be the Internet or some other public or private network. Client computing devices 305 can be connected to network 330 through a network interface, such as by wired or wireless communication. While the connections between server 310 and servers 320 are shown as separate connections, these connections can be any kind of local, wide area, wired, or wireless network, including network 330 or a separate public or private network.

Figure 4:
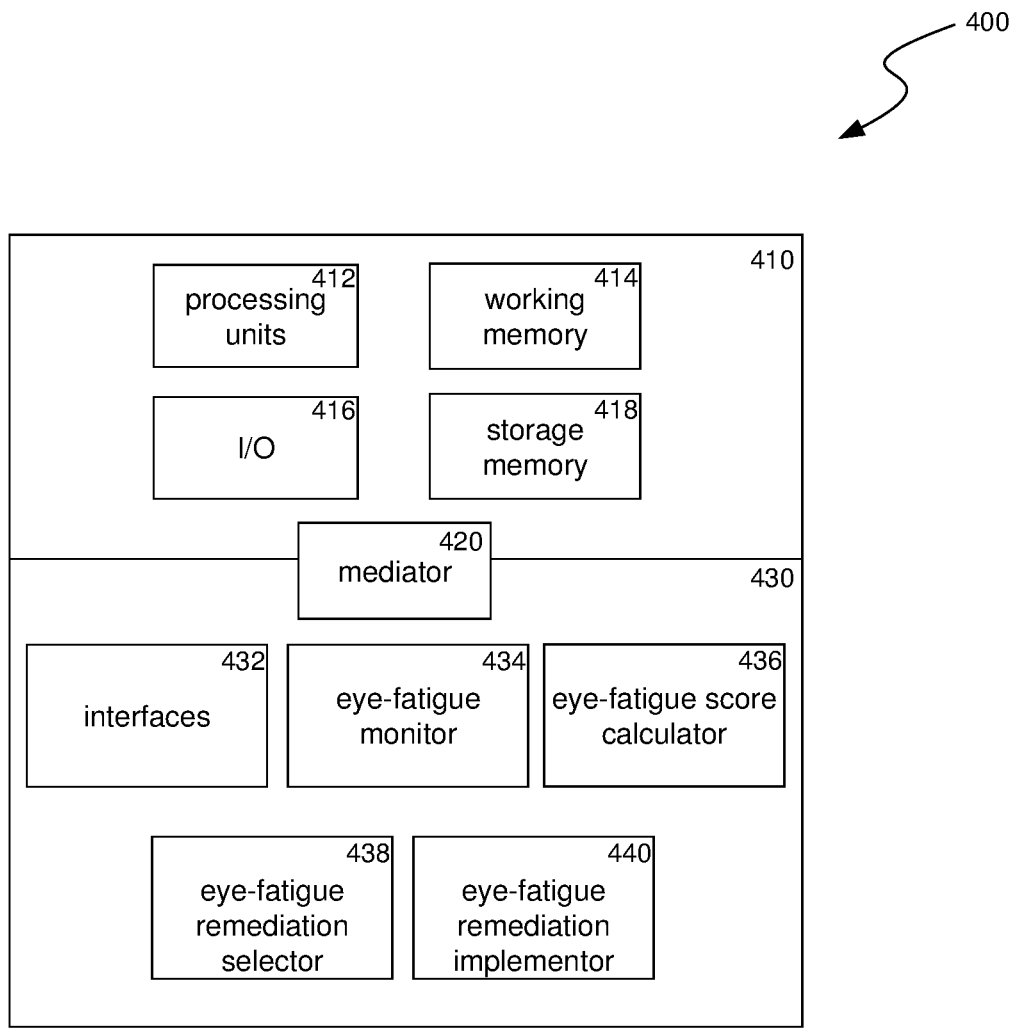
FIG. 4 is a block diagram illustrating components which, in some implementations, can be used in a system employing the disclosed technology.

FIG. 4 is a block diagram illustrating components 400 which, in some implementations, can be used in a system employing the disclosed technology. Components 400 can be included in one device of computing system 100 or can be distributed across multiple of the devices of computing system 100. The components 400 include hardware 410, mediator 420, and specialized components 430. As discussed above, a system implementing the disclosed technology can use various hardware including processing units 412, working memory 414, input and output devices 416 (e.g., cameras, displays, IMU units, network connections, etc.), and storage memory 418. In various implementations, storage memory 418 can be one or more of: local devices, interfaces to remote storage devices, or combinations thereof. For example, storage memory 418 can be one or more hard drives or flash drives accessible through a system bus or can be a cloud storage provider (such as in storage 315 or 325) or other network storage accessible via one or more communications networks. In various implementations, components 400 can be implemented in a client computing device such as client computing devices 305 or on a server computing device, such as server computing device 310 or 320.

Mediator 420 can include components which mediate resources between hardware 410 and specialized components 430. For example, mediator 420 can include an operating system, services, drivers, a basic input output system (BIOS), controller circuits, or other hardware or software systems.

Specialized components 430 can include software or hardware configured to perform operations for monitoring, preventing, and alleviating eye fatigue. Specialized components 430 can include an eye-fatigue monitor 434, an eye-fatigue score calculator 436, an eye-fatigue remediation selector 438, an eye-fatigue remediation implementor 440, and components and APIs which can be used for providing user interfaces, transferring data, and controlling the specialized components, such as interfaces 432. In some implementations, components 400 can be in a computing system that is distributed across multiple computing devices or can be an interface to a server-based application executing one or more of specialized components 430. Although depicted as separate components, specialized components 430 may be logical or other nonphysical differentiations of functions and/or may be submodules or code-blocks of one or more applications.

In various implementations, the eye-fatigue monitor 434 can receive information from real-world sensors (e.g., a camera) and from an XR feed. A camera (possibly associated with an XR system's eye-tracking system) presents information about the user's eye color, amount of swelling near the eye, pupil dilation, or an increased amount of blood flow near the eye. A camera on an HMD 200, 250, if available to the eye-monitoring system, can measure an amount of eye movement, how often the eyes move toward their range limits, and an amount of time the eyes are used. Other sensors can determine a level of eye moisture or an eye temperature. From an XR feed, the eye-fatigue monitor 434 can determine the color and brightness of the content viewed by the user. The eye-monitoring system can also detect from the XR feed when the user makes a gesture indicative of eye fatigue, such as rubbing the eyes or the muscles around the eyes. Additional details on the workings of the eye-fatigue monitor 434 are provided below in relation to block 504 of FIG. 5.

The eye-fatigue score calculator 436 takes the results of the eye-fatigue monitor 434 and assigns a score to them. The calculated score reflects all of the eye-fatigue indicia reported by the eye-fatigue monitor 434 and their severity. A higher score is associated with a higher probability of current or incipient eye fatigue. In some implementations, the eye-fatigue score calculator 436 can compute various scores for different types of eye fatigue, such as for muscle fatigue, sensitivity to brightness, dryness, etc. Additional details of the eye-fatigue score calculator 436 are provided below in relation to block 506 of FIG. 5.

The eye-fatigue remediation selector 438 takes the score(s) from the eye-fatigue score calculator 436 and, in some implementations, information about the monitored indicia that led to that score. It then selects one or more remediation actions from those available in the present implementation. A low score may warrant just a warning message, while a high score could warrant more active intervention such as changing aspects of the user's display content or "spritzing" the eyes. Additional details on the workings of the eye-fatigue remediation selector 438 are provided below in relation to block 508 of FIG. 5.

The eye-fatigue remediation implementor 440 receives the information about the selected one or more remediation actions and implements them. If the actions include eye spritzing or muscle massaging, then the eye-fatigue implementor 440 directs the HMD 700 (see FIG. 7 and accompanying text) to perform those actions. If the selected remediation actions include changing aspects of the content displayed to the user, commands to do so are sent through the I/O channels 416 to an XR system feed or directly to the user's display or audio device. Additional details on the eye-fatigue remediation implementor 440 are provided below in relation to block 510 of FIG. 5.

Those skilled in the art will appreciate that the components illustrated in FIGS. 1-4 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 5:
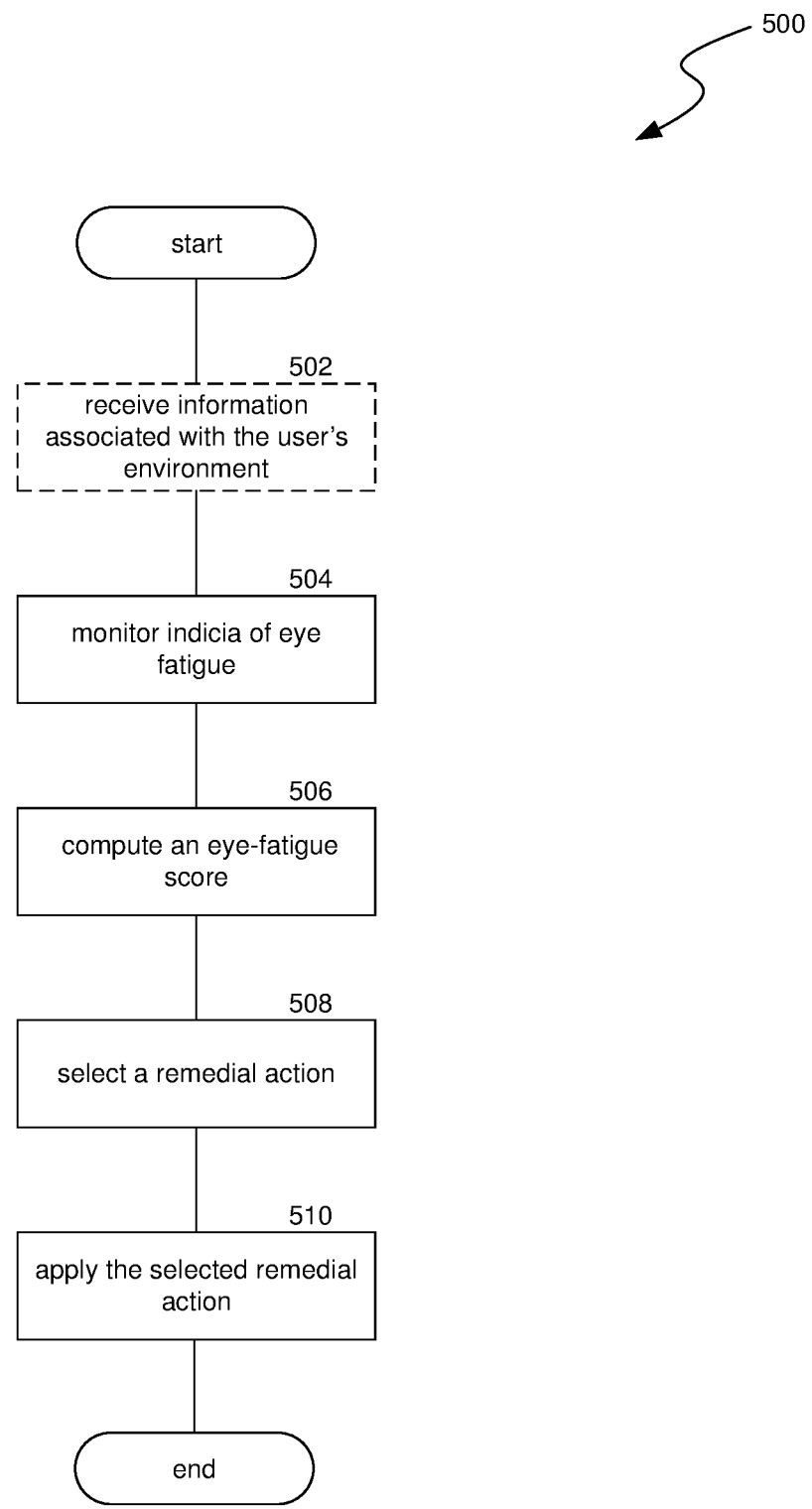
FIG. 5 is a flow diagram illustrating a process used in some implementations of the present technology for monitoring and alleviating or preventing eye fatigue.

FIG. 5 is a flow diagram illustrating a process 500 used in some implementations for preventing or alleviating eye fatigue in a user. In some implementations, this process 500 runs as long as the user is in a suitable environment. It may be invoked when, for example, a user turns on an HMD 200, 250 and runs as long as that HMD 200, 250 is active. In some implementations, process 500 can be performed on a user device (e.g., the user's HMD 200, 250). In other implementations, process 500 can be performed on a server system, which can, in-turn, receive information from, and provide controls to, such a user device.

While any block can be removed or rearranged in various implementations, block 502 is shown in dashed lines to indicate there are specific instances where block 502 is skipped. At block 502, the process 500 receives information about a user's current environment. As seen by the user, the user's current environment may be purely real, purely virtual, or a combination of the two. The types of environmental information can include visual information (that is, what the user is seeing given the direction and focus of his gaze), air temperature, humidity level, etc. Some implementations focus on specific types of information in this step and mostly ignore other types.

In block 504, the process 500 monitors indicia of eye fatigue. Various implementations support various sets of indicia. A full set of indicia would include at least an amount of eye movement, how often an eye moves toward its range limits, an amount of time an eye is used, eye moisture, eye color, amount of swelling near an eye, amount of blood flow near an eye, pupil dilation, eye temperature, color of content viewed, brightness of content viewed, a user gesture, or any combination of these.

In various implementations, the process 500 can receive information from real-world sensors (e.g., a camera) and from an XR feed to simultaneously monitor several indicia. A camera (possibly associated with an XR system's eye-tracking system) presents information about the user's eye color, amount of swelling near the eye, pupil dilation, or an increased amount of blood flow near the eye. A camera on an HMD 200, 250, if available to the process 500, can measure an amount of eye movement, how often the eyes move toward their range limits, and an amount of time the eyes are used. Other sensors determine a level of eye moisture or an eye temperature. Some implementations have access to measurements of the current air temperature and humidity level.

From an XR feed, the process 500 can determine the color and brightness of content viewed by the user. In some implementations, the process 500 can also detect from the XR feed when the user makes a gesture indicative of eye fatigue, such as rubbing the eyes or the muscles around the eyes.

At block 506, the process 500 calculates one or more eye-fatigue scores based on the eye-fatigue indicia available from whatever sensors are supported by the current implementation. Details of the calculation depend upon details of the supported set of sensors. In a very simple implementation, each sensor provides either a "Yes, I detect eye-fatigue" or a "No, eyes are fine for now" result. If any result is "Yes," then the calculated score is made high enough that the process 500 moves on to the remediation selection block 508. In a more sophisticated version, some sensors provide a range of values. The process 500 considers each sensor value in the context of its potential range and scores accordingly. For example, eye irritation (e.g., determined by redness) may be scored from 1 to 10, with anything above 4 meriting a high score. The monitored indicia may be compared to baseline values, with their departure from the baseline values an indication of their severity. A baseline may be based on information of a general population or on previous observations of this particular user. For example, the resting (that is, un-fatigued) color of this user's eyes can be recorded as a baseline, with an indicium being the departure of the user's eye color from that baseline.

Various sensors may also be weighted differently, either separately or in any combination. For example, a long usage period (as reported by an HMD 200, 250) when combined with a measured low humidity level and high air temperature, could result in a high score regardless of the results of the other indicia sensors. Detecting that the user is rubbing her eyes may be associated with the highest possible score, again regardless of the other indicia sensors. In general, the threshold score for proceeding to remediation should be set low enough that eye fatigue is caught early when it can still be readily addressed.

Some implementations generate multiple scores for multiple aspects of eye fatigue, the differing scores possibly based on differing subsets of eye-fatigue indicia. For example, one score may reflect the possibility of muscle fatigue based on total eye movements over time, while another score reflects the possibility of increasing sensitivity to brightness based on the brightness of the viewed content over time. A third score can reflect the possibility of dryness in the eye based on viewing the eye for signs of moisture or on noting a user's gesture that may be responsive to eye dryness.

In block 508, the process 500 considers the calculated eye-fatigue score and selects one or more remediation actions. Various implementations support various remediations, which may include sending a notification to the user warning of current or incipient eye fatigue. Invoking the eye-muscle massagers 706 or eye-drop spritzers 704 (see FIG. 7 and accompanying text) is pretty invasive so even if the current implementation supports these remediation actions, they may only be used in response to a relatively high fatigue score.

In some implementations, when selecting a remediation in block 508, the process 500 considers the score and also considers which sensors' readings led to that score. For example, if the process 500 sees a high score based on a combination of (i) a long period of viewing and (ii) the viewed content having strong blues or greens, it might select the remediation of changing the color palette of the content presented to the user, shifting it slightly toward red. This remediation is only selected for systems that can direct commands to the user's display. In these and similar situations, the process 500 can also decrease the brightness of the display.

In block 510, the process 500 implements the one or more selected remedial actions. If the actions include eye spritzing or muscle massaging, then the process 500 directs the HMD 700 (FIG. 7) to perform those actions. The spritzers 704 apply a small amount of eye drops to the fatigued eyes. The motor-driven muscle massagers 706 are in touch with the area around the eyes. Their massaging action may lessen the fatigue in those muscles. If the selected remediation actions include changing aspects of the content displayed to the user, then the process 500 sends commands to do so through an XR system feed or directly to the user's display device. (See FIGS. 8 and 9 for an example of this remedial action.) A warning message to the user is sent through those same channels and displayed on the user's screen.

The process 500 may be repeated periodically while the user continues to use the HMD 200, 250.

Figure 6:
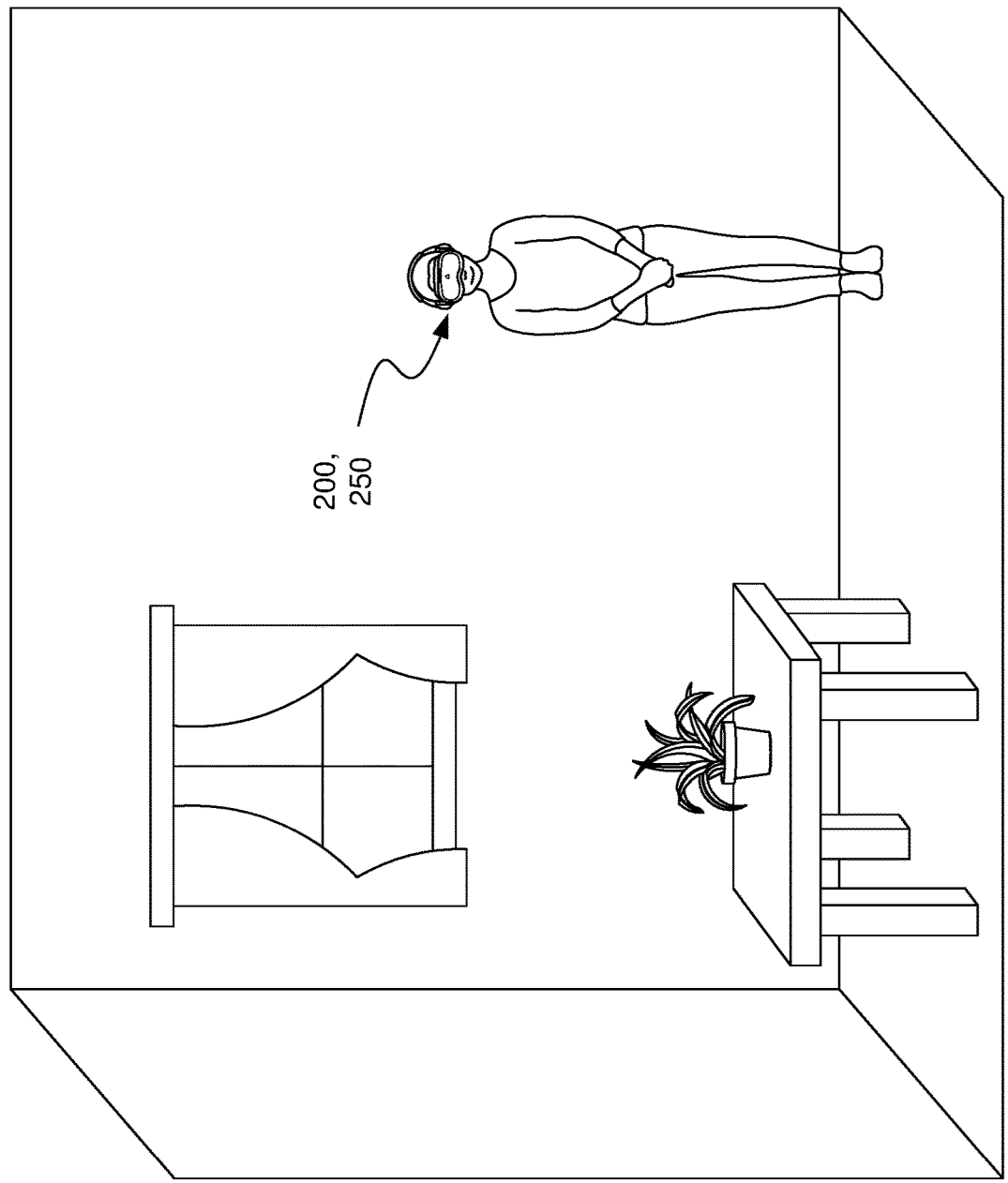
FIG. 6 is a conceptual diagram of a user wearing an HMD.

FIG. 6 shows a user wearing an HMD 200, 250. Her view may include aspects of the real world, and it may include virtual aspects as well. Regardless of the nature of her viewed world, she exists in a physical world that includes her, her HMD 200, 250, her eyes (subject to fatigue), and the air around her with its temperature and humidity. As she views her world, the eye-monitoring process 500 monitors her for indicia of eye fatigue (as described in relation to block 504 of FIG. 5) and from those indicia computes one or more eye-fatigue scores (block 506). As described above, the process 500 considers different aspects of eye fatigue (e.g., muscle fatigue, light sensitivity, or eye moisture level) and may compute different eye-fatigue scores for these different aspects.

Figure 7:
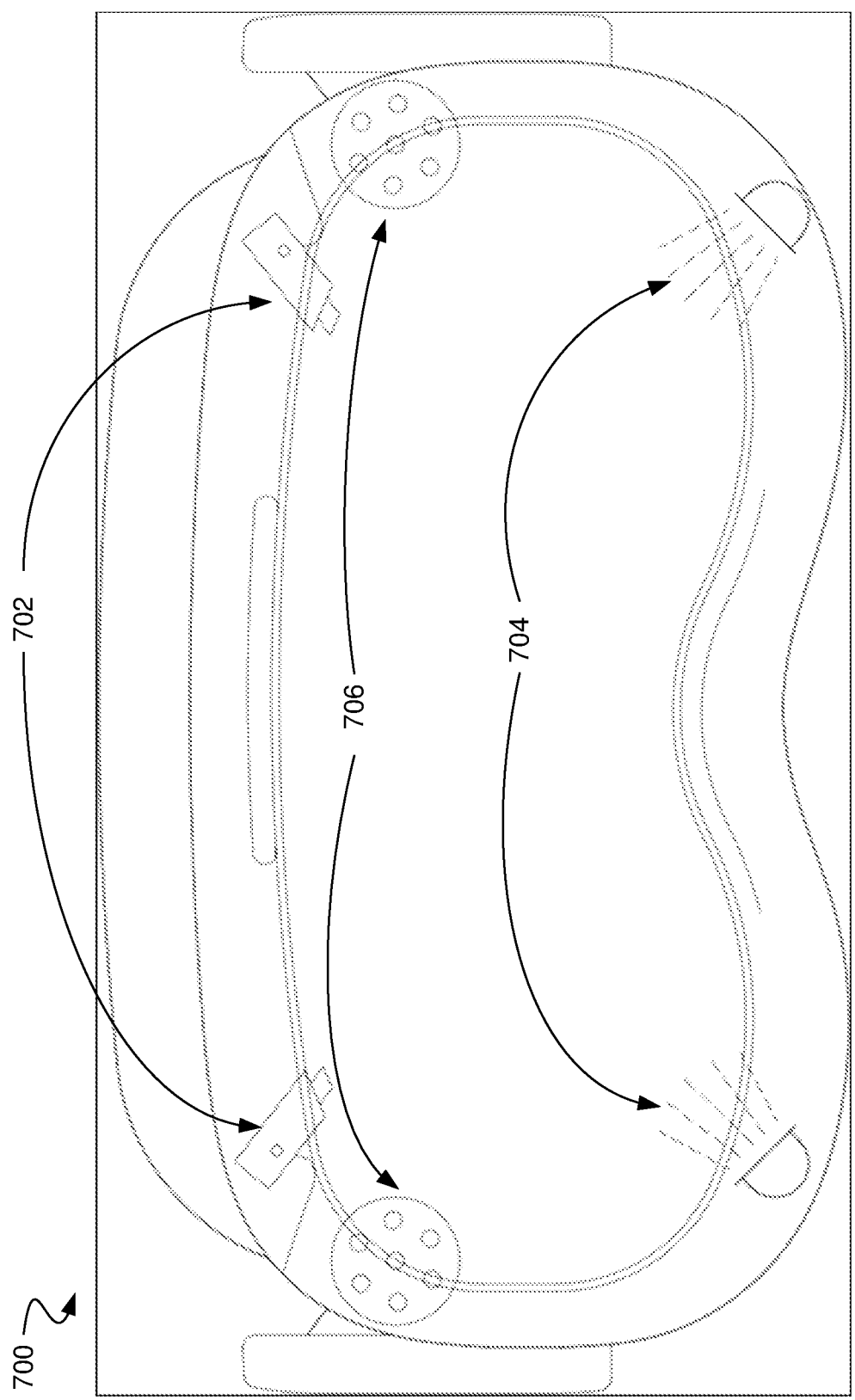
FIG. 7 is a wire diagram illustrating a headset which can be used in some implementations of the present technology.

The user's HMD may be as described above, but in some situations it includes the features of the HMD 700 of FIG. 7. This HMD 700 includes cameras 702 that view her eyes and the areas around her eyes. In some implementations, these cameras 702 are part of an eye-tracking system in the HMD 700. The cameras 702 monitor the eyes for indicia of eye fatigue as described above in relation to block 504 of FIG. 5.

Also included in HMD 700 can be eye spritzers 704. As described above in relation to block 510 of FIG. 5, the eye-monitoring process 500 can command these spritzers to spray a small amount of eye-moisturizer to relieve fatigued eyes.

In some implementations, the HMD 700 also includes muscle massagers 706. As also described above in relation to block 510 of FIG. 5, these motor-driven or vibrating muscle massagers 706 are in touch with the area around the eyes of the wearer of the HMD 700. Upon command, they massage the muscles which may lessen fatigue in those muscles.

Figure 8:
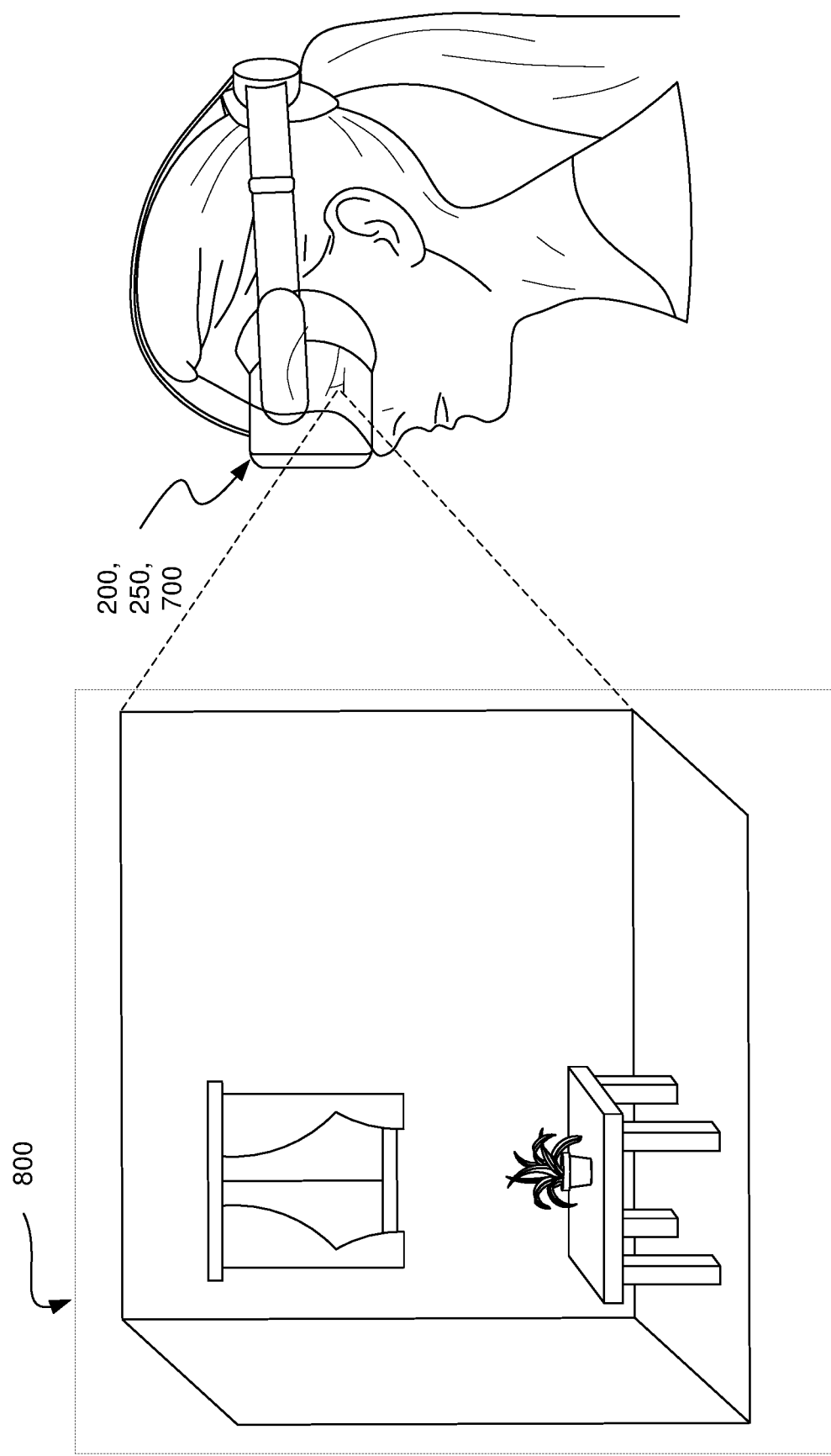
FIG. 8 is a conceptual diagram of a user wearing an HMD to view a scene.

In FIG. 8, the user is wearing an HMD 200, 250, 700 (that is, one with or without spritzers 704 and muscle massagers 706). The user is viewing a scene 800 that may be real, virtual, or a combination. For real objects in the scene 800 (if any), FIG. 8 portrays the user looking through the lenses of her HMD 200, 250, 700 at those real objects. Virtual objects in the scene 800 (if any) are displayed within the user's HMD 200, 250, 700, and FIG. 8 portrays the illusion of viewing those virtual objects through the lenses of the HMD 200, 250, 700.

In all cases, the scene 800 that the user is viewing is produced by at least one light-emitting display screen. She may be viewing a real-world television or smartphone, for example. Instead of or in addition to that, she may be viewing the scene 800 through an electronic display 245 (FIG. 2A) or pass-through display 258 (FIG. 2B) of her HMD 200, 250, 700.

In FIG. 8, although the eye-monitoring process 500 is monitoring possible indicia of eye fatigue (block 504 of FIG. 5) and computing one or more eye-fatigue scores (block 506), none of those scores (either separately or in any combination) has risen to a level that triggers the process 500 to take remedial action. Thus, the user's view of the display screen or screens in scene 800 is unaltered by the eye-monitoring process 500.

If, however, the eye-fatigue scores rise to a threshold level based on the process 500's detection of indicia of eye fatigue in the user, and if the process 500 (*i*) notes that the user has been viewing content, real or virtual, that is potentially fatiguing (a large proportion of strong blues in the scene 800, for example), and if the process 500 (*ii*) can send commands to the display screen viewed by the user, then the process 500 may select to remediate her eye fatigue by changing at least one aspect of the screen's content as viewed by the user.

Figure 9:
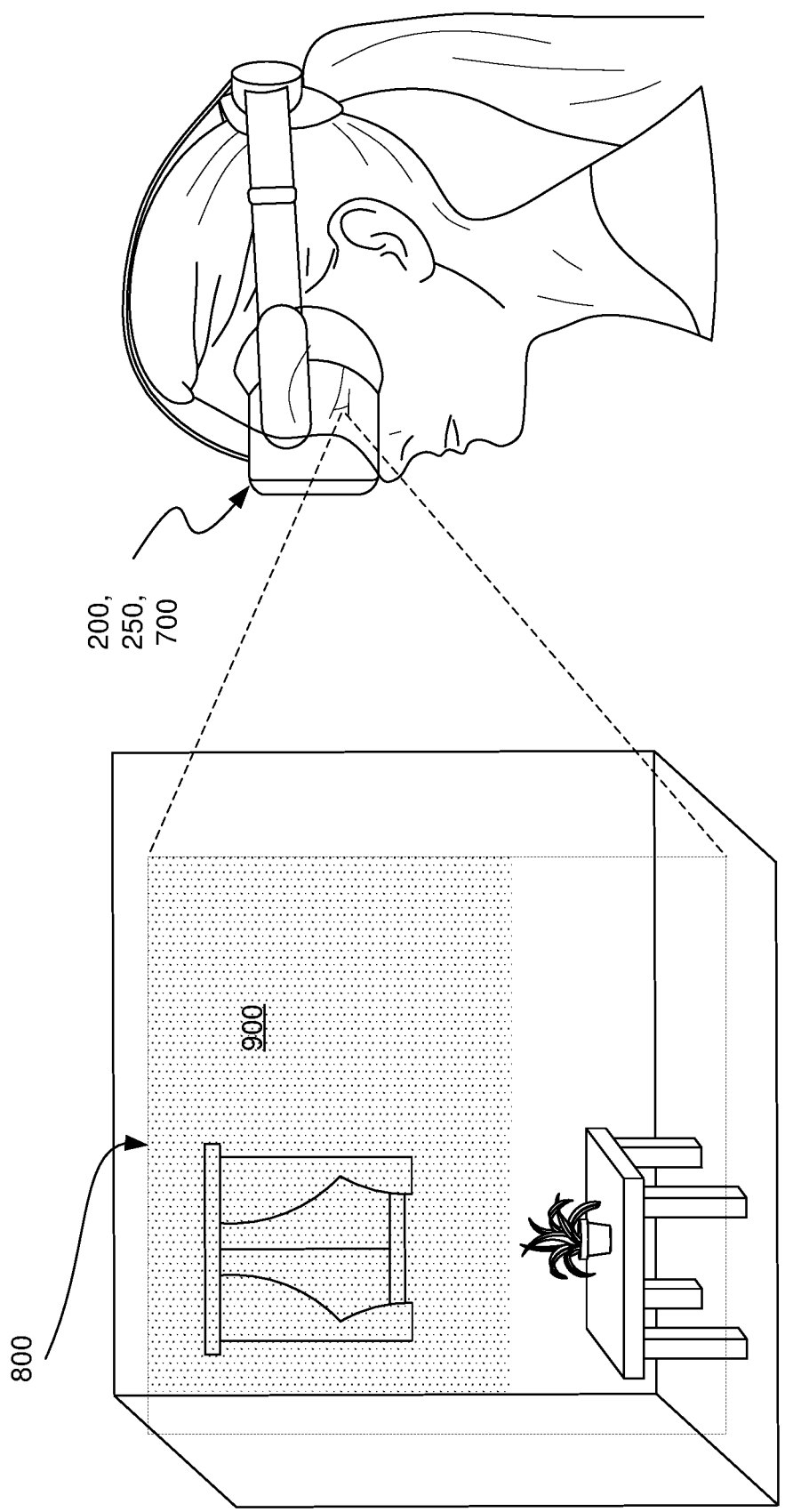
FIG. 9 is a conceptual diagram of a user wearing an HMD to view a scene altered to reduce eye fatigue.

FIG. 9 shows the same scenario as in FIG. 8, but here the eye-monitoring process 500 has changed aspects of the scene 800 as viewed by the user. Here, the monitored indicia show that the user has been moving her eyes to the edges of the scene 800 often enough to cause eye fatigue. The process 500 has responded (blocks 508, 510 of FIG. 5) by slightly narrowing the scene 800 to prevent further extreme eye movements.

In addition, the eye-monitoring process 500 notes that the upper portion 900 of the scene 800 is such as to trigger eye fatigue. In some cases, this is caused by extremes of brightness or of a very strong color palette (too many hard blues). The shading in FIG. 9 indicates that the process 500 changed the color palette or decreased the brightness of that portion 900 of the viewed content to relieve the user's eye fatigue. In this example, the process 500 notes no problem with the lower portion of the scene 800, so it is left alone (indicated by the lack of shading in FIG. 9).

If the eye-fatigue scores (block 506 of FIG. 5) so indicate, then the eye-monitoring process 500 may instead of or in addition to changing the view 800 invoke the eye spritzers 704 or muscle massagers 706 if the user's HMD is so equipped.

Reference in this specification to "implementations" (e.g., "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle-specified number of items, or that an item under comparison has a value within a middle-specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

We claim:

1. A method for a computer system to address eye fatigue in a user, the method comprising:
    monitoring one or more indicia of eye fatigue of the user, a first eye fatigue indicia comprising eye movement to a range limit and a second eye fatigue indicia comprising a user gesture, wherein at least a portion of the one or more indicia of eye fatigue are monitored while an XR system displays an environment to the user;
    computing eye-fatigue scores by weighting and combining the monitored eye-fatigue indicia, wherein a first eye fatigue score relates to muscle fatigue and a second eye fatigue score relates to content fatigue;
    selecting one or more remedial actions based on the computed eye-fatigue scores; and
    applying selected remedial actions including one or more of:
        massaging muscles near an eye;
        narrowing a scene presented to the user via the XR system; or
        any combination thereof.

2. The method of claim 1 further comprising receiving information associated with the user's environment, wherein the user's environment comprises an XR-generated environment, and wherein the applying selected remedial actions includes a modification to the XR-generated environment based on the received information associated with the user's environment.

3. The method of claim 1 wherein the indicia of eye fatigue are one or more of: amount of eye movement, amount of time an eye is used, eye moisture, eye redness, amount of swelling near an eye, amount of blood flow near an eye, pupil dilation, eye temperature, color of content viewed, brightness of content viewed, or any combination thereof.

4. The method of claim 1 wherein the weighting is based, at least in part, on one or more of: expected muscle fatigue, expected over stimulation, expected dryness, comparison to a baseline value, or any combination thereof.

5. The method of claim 4 wherein the baseline value is based, at least in part, on one or more of: a representative value of a population, a value associated with the user, or any combination thereof.

6. The method of claim 1,
    wherein the selected remedial action comprises massaging muscles near the eye; and
    wherein the massaging muscles near the eye comprises massaging performed by a headset worn by the user.

7. The method of claim 1,
    wherein the selected remedial action comprises narrowing the scene presented to the user via the XR system; and
    wherein the narrowing the scene presented to the user via the XR system further includes directing a visual information presenter to change one or more of: an intensity of brightness of content viewed by the user, a color palette of content viewed by the user, or any combination thereof.

8. The method of claim 1 further comprising alerting the user to a potential of eye fatigue.

9. A computer-readable storage medium storing instructions that, when executed by a computing system, cause the computing system to perform a process for addressing eye fatigue in a user, the process comprising:
   monitoring one or more indicia of eye fatigue of the user, a first eye fatigue indicia comprising eye movement to a range limit and a second eye fatigue indicia comprising a user gesture, wherein at least a portion of the one or more indicia of eye fatigue are monitored while an XR system displays an environment to the user;
   computing eye-fatigue scores by weighting and combining monitored eye-fatigue indicia, wherein a first eye fatigue score relates to muscle fatigue and a second eye fatigue score relates to content fatigue;
   selecting one or more remedial actions based on the computed eye-fatigue scores; and
   applying selected remedial actions including one or more of:
      massaging muscles near an eye;
      narrowing a scene presented to the user via the XR system; or
      any combination thereof.

10. The computer-readable storage medium of claim 9 wherein the indicia are one or more of: amount of eye movement, amount of time an eye is used, eye moisture, eye color, amount of swelling near an eye, amount of blood flow near an eye, pupil dilation, eye temperature, color of content viewed, brightness of content viewed, or any combination thereof.

11. The computer-readable storage medium of claim 9, wherein the selected remedial action comprises narrowing the scene presented to the user via the XR system; and
    wherein the narrowing the scene presented to the user via the XR system further includes directing a visual information presenter to change one or more of: an intensity of brightness of content viewed by the user, a color palette of content viewed by the user, or any combination thereof.

12. The computer-readable storage medium of claim 9 wherein the process further comprises alerting the user to a potential of eye fatigue.

13. A computing system for addressing eye fatigue in a user, the computing system comprising:
    one or more processors; and
    one or more memories storing instructions that, when executed by the one or more processors, cause the computing system to perform a process comprising:
       monitoring one or more indicia of eye fatigue of the user, a first eye fatigue indicia comprising eye movement to a range limit and a second eye fatigue indicia comprising a user gesture, wherein at least a portion of the one or more indicia of eye fatigue are monitored while an XR system displays an environment to the user;
       computing eye-fatigue scores by weighting and combining monitored eye-fatigue indicia, wherein a first eye fatigue score relates to muscle fatigue and a second eye fatigue score relates to content fatigue;
       selecting one or more remedial actions based on the computed eye-fatigue scores; and
       applying selected remedial actions including one or more of:
          massaging muscles near an eye;
          narrowing a scene presented to the user via the XR system; or
          any combination thereof.

14. The computing system of claim 13 wherein the indicia are one or more of: amount of eye movement, amount of time an eye is used, eye moisture, eye color, amount of swelling near an eye, amount of blood flow near an eye, pupil dilation, eye temperature, color of content viewed, brightness of content viewed, or any combination thereof.

15. The computing system of claim 13 wherein the computing system is the XR system.

16. The computing system of claim 13 further comprising an information-receiving device which includes one or more of: a contact lens, a camera, a head-mounted display, a feed from the XR system, or any combination thereof, wherein the information-receiving device generates information associated with the monitoring of one or more indicia of eye fatigue of the user.

17. The computing system of claim 13 further comprising an output device which includes one or more of: a contact lens, an eye-muscle massager, a display screen, or any combination thereof, wherein the output device performs the selected remedial action.

18. The computing system of claim 13 wherein the process further comprises alerting the user to a potential of eye fatigue.

19. The method of claim 1 wherein the second eye fatigue score is based at least in part on the first eye fatigue indicia and a frequency with which the monitored eye movement moves toward the range limit.

20. The computing system of claim 19 wherein the narrowing of the scene presented to the user via the XR system is selected as the remedial action based on comparing the second eye fatigue score to a threshold.

* * * * *